(12) United States Patent
Jin et al.

(10) Patent No.: US 10,827,992 B2
(45) Date of Patent: Nov. 10, 2020

(54) ENERGY-DISCRIMINATING PHOTON-COUNTING DETECTOR AND THE USE THEREOF

(71) Applicant: GENERAL ELECTRIC COMPANY, Schenectady, NY (US)

(72) Inventors: Yannan Jin, Schenectady, NY (US); Peter Michael Edic, Albany, NY (US); Xue Rui, Clifton Park, NY (US); Geng Fu, Rexford, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 16/511,218

(22) Filed: Jul. 15, 2019

(65) Prior Publication Data
US 2019/0336091 A1 Nov. 7, 2019

Related U.S. Application Data

(63) Continuation of application No. 15/400,798, filed on Jan. 6, 2017, now Pat. No. 10,398,394.

(51) Int. Cl.
| | |
|---|---|
| *A61B 6/00* | (2006.01) |
| *A61B 6/03* | (2006.01) |
| *G01T 1/29* | (2006.01) |
| *G01T 1/36* | (2006.01) |
| *G01V 5/00* | (2006.01) |
| *G06T 11/00* | (2006.01) |

(52) U.S. Cl.
CPC .......... *A61B 6/4241* (2013.01); *A61B 6/032* (2013.01); *A61B 6/481* (2013.01); *A61B 6/482* (2013.01); *A61B 6/5205* (2013.01); *A61B 6/5217* (2013.01); *A61B 6/5282* (2013.01); *A61B 6/585* (2013.01); *G01T 1/2985* (2013.01); *G01T 1/36* (2013.01); *G01V 5/0016* (2013.01); *G06T 11/006* (2013.01); *G06T 2211/408* (2013.01)

(58) Field of Classification Search
CPC ........ A61B 6/4241; G01T 1/36; G06T 11/005
See application file for complete search history.

(56) References Cited

U.S. PATENT DOCUMENTS

| | | | |
|---|---|---|---|
| 7,208,739 | B1 | 4/2007 | Yanoff et al. |
| 7,486,764 | B2 | 2/2009 | Tkaczyk et al. |
| 7,613,274 | B2 | 11/2009 | Tkaczyk et al. |

(Continued)

FOREIGN PATENT DOCUMENTS

| | | |
|---|---|---|
| WO | 2016106348 A1 | 6/2016 |

OTHER PUBLICATIONS

Ponchut, Cyril; "Correction of the Charge Sharing in Photon-Counting Pixel Detector Data", Nuclear Instruments and Methods in Physics Research Section A: Accelerators, Spectrometers, Detectors and Associated Equipment, vol. 591, Issue 1, pp. 311-313, 2008.

(Continued)

*Primary Examiner* — Dani Fox

(57) ABSTRACT

The present approaches relates to the use of silicon-based energy-discriminating, photon-counting detectors, such as for use in X-ray based imaging including computed tomography. The described approaches address the resolution and classification of X-ray photons affected by Compton scatter, which may be detected as having energy levels below their proper level due to collision or deflection events.

16 Claims, 8 Drawing Sheets

(56) References Cited

U.S. PATENT DOCUMENTS

| | | |
|---|---|---|
| 7,916,836 B2 | 3/2011 | Tkaczyk et al. |
| 8,183,535 B2 | 5/2012 | Danielsson et al. |
| 8,378,310 B2 | 2/2013 | Bornefalk et al. |
| 9,036,879 B2 | 5/2015 | Mendonca et al. |
| 2010/0215230 A1* | 8/2010 | Bornefalk ............ G06T 11/005 382/128 |
| 2016/0193366 A1 | 7/2016 | Yeh et al. |

OTHER PUBLICATIONS

Yveborg, Moa, et al.; "Theoretical Comparison of a Dual Energy System and Photon Counting Silicon Detector Used for Material Quantification in Spectral CT", IEEE Transactions on Medical Imaging, vol. 34, Issue 3, pp. 796-806, Oct. 14, 2014.

Liu, Xuejin, et al.; "Energy Calibration of a Silicon-strip Detector for Photon-counting Spectral CT by Direct Usage of the X-ray Tube Spectrum", IEEE Transactions on Nuclear Science, vol. 62, Issue 1, pp. 68-75, Jan. 8, 2015.

McCollough, Ph.D., Cynthia H., et al.; "Dual- and Multi-Energy Computed Tomography: Principles, Technical Approaches, and Clinical Applications", Radiology, vol. 276, Issue 3, pp. 637-653, Sep. 2015.

Liu, Xuejin, et al.; "Spectral Response Model for a Multibin Photon-Counting Spectral Computed Tomography Detector and its Applications", Journal of Medical Imaging, vol. 2, Issue 3, Sep. 11, 2015.

\* cited by examiner

ENERGY-DISCRIMINATING PHOTON-COUNTING DETECTOR AND THE USE THEREOF

CROSS-REFERENCE TO RELATED APPLICATION

This application claims priority to and the benefit of U.S. patent application Ser. No. 15/400,798, entitled "ENERGY-DISCRIMINATING PHOTON-COUNTING DETECTOR AND THE USE THEREOF", filed Jan. 6, 2017, which is herein incorporated by reference in its entirety for all purposes.

BACKGROUND

The subject matter disclosed herein relates to the use of energy-discriminating photon-counting detectors, including silicon-based photon-counting detectors, such as in material decomposition contexts.

Non-invasive imaging technologies allow images of the internal structures or features of a subject (patient, manufactured good, baggage, package, or passenger) to be obtained non-invasively. In particular, such non-invasive imaging technologies rely on various physical principles, such as the differential transmission of X-rays through the target volume or the reflection of acoustic waves, to acquire data and to construct images or otherwise represent the internal features of the subject.

For example, in X-ray-based imaging technologies, X-ray radiation spans a subject of interest, such as a human patient, and a portion of the radiation impacts a detector where the intensity data is collected. In digital X-ray systems, a detector produces signals representative of the amount or intensity of radiation impacting discrete pixel regions of a detector surface. The signals may then be processed to generate an image that may be displayed for review.

In one such X-ray based technique, known as computed tomography (CT), a scanner may project fan-shaped or cone-shaped X-ray beams from an X-ray source at numerous view angle positions about an object being imaged, such as a patient. The X-ray beams are attenuated as they traverse the object and are detected by a set of detector elements which produce signals representing the intensity of the incident X-ray intensity on the detector. The signals are processed to produce data representing the line integrals of the linear attenuation coefficients of the object along the X-ray paths. These signals are typically called "projection data" or just "projections". By using reconstruction techniques, such as filtered backprojection, images may be generated that represent a volume or a volumetric rendering of a region of interest of the patient or imaged object. In a medical context, pathologies or other structures of interest may then be located or identified from the reconstructed images or rendered volume.

Conventionally, radiation detectors used in these types of imaging techniques operate in an energy-integrating (i.e., readout of the total integrated energy deposited during an acquisition interval) mode or a photon-counting (each individual X-ray photon is detected and its energy characterized) mode. Energy integration is the conventional mode for X-ray detectors in most clinical applications. However, energy-integrating readout approaches operate poorly in low-flux imaging applications, where electronic noise associated with the detector, including the readout operation, may overwhelm the available signal. As evident to those skilled in the art, photon-counting detectors offer other benefits relative to energy-integrating detectors, such as improved resolution, the ability to improve contrast-to-noise ratio by optimally weighting detected photons, the ability to better delineate materials in the X-ray beam, and so on.

In some applications, photon counts are of more interest than the total integrated energy information associated with energy-integrating approaches. Conventional scintillator-based photon-counting detectors for positron emission tomography (PET) utilize silicon photomultipliers (SiPMs) that are expensive and not practical for high count rate applications such as CT. Further, some photon-counting approaches may be limited in the type of information they produce, such as yielding only raw photon count data without information pertaining to the energy of the detected photons.

In contrast, certain techniques, such as dual-energy (e.g., high- and low-energy imaging) and/or material-decomposition imaging, benefit not only from photon counts in a general sense, but from obtaining spectral information for a given exposure interval. That is, such techniques utilize photon counts that are broken down into respective energy bins, and thus discriminate between photon events at different energies, thereby determining and counting the number of photons observed at different photon energy ranges. To address this need, certain energy-discriminating, photon-counting X-ray detector technologies may be employed. In certain instances, such approaches employ a detection medium that directly converts incident X-rays to measurable signal (i.e., electron-hole pairs generated using direct conversion materials), as opposed to techniques employing a scintillator-based intermediary conversion and subsequent detection of the generated optical photons.

Examples of such direct conversion materials include cadmium zinc telluride (CZT) and cadmium telluride (CdTe). However, these materials are not capable of higher incident count rates that may be of interest in practice. Alternatively, silicon strips may be employed as part of a direct-conversion, energy-discriminating, photon-counting detector. Such silicon strip based detectors may be capable of higher incident photon count rates than CZT or CdTe detectors. However, the primary attenuation mechanism with silicon strip based detectors is Compton scattering, which can substantially decrease dose efficiency and spectral fidelity in the associated energy response function of the detector. In particular, such a Compton scatter event typically results in an X-ray photon transferring a portion of its energy to a particle with which it interacts in passing (i.e., the deflecting or scatting particle), thereby changing (i.e., decreasing) the energy of the X-ray photon as well as potentially changing its trajectory.

BRIEF DESCRIPTION

In one embodiment, an X-ray based imaging system is provided. In accordance with this embodiment, the X-ray based imaging system includes an X-ray source configured to emit X-rays at one or more energy spectra and an X-ray detector comprising a silicon-based direct-conversion material. The X-ray detector is configured to generate signals in response to the transmitted X-rays during operation, where the signals correspond to photon counts observed at different energy levels for each exposure interval. The X-ray based imaging system also includes a processing component configured to receive the signals from the X-ray detector and to bin the photon count data for at least one respective energy spectrum based on observed energy levels into one of a primary high-energy bin above a first threshold; a low-energy bin between a second threshold and the first threshold; and a secondary high-energy bin above a discard threshold and below the second threshold. The processing component is further configured to generate one or more images using high-energy photon counts derived for the primary high-energy bin and secondary high-energy bin and using the low-energy photon counts in the low-energy bin.

In another embodiment, an X-ray based imaging system is provided. In accordance with this embodiment, the X-ray based imaging system includes an X-ray source configured to emit X-rays at one or more energy spectra and an X-ray detector comprising a silicon-based direct-conversion material. The X-ray detector is configured to generate signals in response to the transmitted X-rays during operation where the signals correspond to photon counts observed at different energy levels for each exposure interval. The X-ray based imaging system also includes a processing component configured to receive the signals from the X-ray detector and to bin the photon count data for at least one respective transmitted energy spectrum based on observed energy levels into one of a primary high-energy bin above a first threshold, a low-energy bin between a second threshold and the first threshold, a secondary high-energy bin between a third threshold and the second threshold, and an unresolved bin between an electronic noise threshold and the third threshold. The processing component is further configured to generate corrected high-energy photon count data and corrected low-energy photon count data based on the photon counts in the unresolved bin and to generate one or more images using the corrected high-energy photon count data and low-energy photon count data.

In a further embodiment, a method for resolving X-ray photon count data is provided. In accordance with this method, a measured transmitted X-ray spectrum is acquired for an object by measuring X-ray photons traversing the object. A low-energy photon-count, a high-energy photon-count, and an unresolved energy photon count are determined based on the measured transmitted spectrum. An initial material decomposition is performed using the low-energy photon count and the high-energy photon count to generate an initial water area density estimate and an initial iodine area density estimate. A simulated transmitted spectrum is generated using a simulated spectrum and the attenuation from the initial water area density estimate and the initial iodine area density estimate. Based upon the simulated transmitted spectrum and the unresolved-energy photon-count, a low-energy photon count correction and a high-energy photon count correction are generated. The low-energy photon count is corrected using the low-energy photon count correction to generate a corrected low-energy photon count and the high-energy photon count is corrected using the high-energy photon count correction to generate a corrected high-energy photon-count. A subsequent material decomposition is performed using the corrected low-energy photon count and the corrected high-energy photon count to generate a corrected water area density estimate and a corrected iodine area density estimate.

In another embodiment, a method for resolving X-ray photon count data is provided. In accordance with this method, a measured transmitted spectrum is acquired for an object by measuring transmission of X-ray photons through the object. A high-energy photon count is determined by considering photons above a low-energy/high-energy threshold, and those photons undergoing Compton scattering and resulting in a detected energy above the Compton edge of the low-energy/high-energy threshold and below the Compton edge of the highest energy photon in the X-ray beam. A low-energy photon count is determined by considering photons above the Compton edge of the highest energy photon in the X-ray beam and below the low-energy/high-energy threshold. Material decomposition is performed using the low-energy photon count and the high-energy photon count to generate a water area density estimate and an iodine area density estimate.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
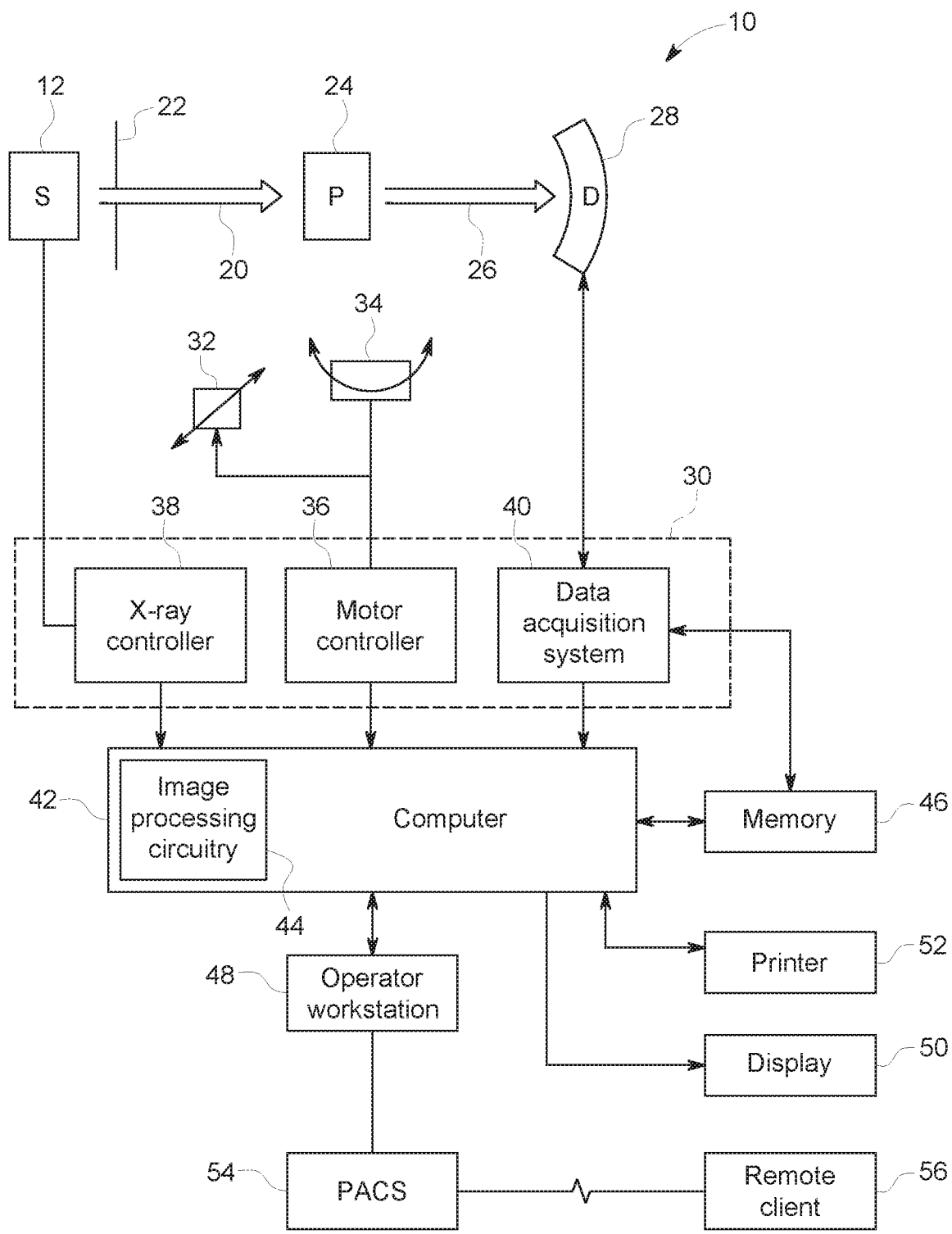
FIG. 1 is a schematic illustration of an embodiment of a computed tomography (CT) system configured to acquire CT images of a patient and process the images in accordance with aspects of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the following discussion is generally provided in the context of medical imaging, it should be appreciated that the present techniques are not limited to such medical contexts. Indeed, the provision of examples and explanations in such a medical context is only to facilitate explanation by providing instances of real-world implementations and applications. However, the present approaches may also be utilized in other contexts, such as the non-destructive inspection of manufactured parts or goods (i.e., quality control or quality review applications), and/or the non-invasive inspection of packages, boxes, luggage, and so forth (i.e., security or screening applications). In general, the present approaches may be desirable in any imaging or screening context in which energy discrimination in a photon-counting context is desirable.

As discussed herein, energy-resolved, photon-counting detectors can provide spectral information that is not available with conventional energy-integrating detectors. One type of energy-discriminating, photon-counting detection technology employs silicon strips as a direct-conversion sensor material. Use of silicon as the direct-conversion material may provide a higher count rate capability than may be obtained with other direct-conversion materials, such as CZT or CdTe, but comes at a potential cost of decreased spectral fidelity due to the Compton absorption mechanism. In particular, due to the relatively low atomic number of silicon compared to CZT and CdTe, Compton scattering dominates as the absorption mechanism, whereas photoelectric absorption dominates in CZT and CdTe direct-conversion sensors. Consequently, at higher X-ray energies for a silicon direct-conversion sensor, a greater portion of X-ray photons exhibit Compton effects (i.e., partial energy loss due to a scattering interaction) relative to photoelectric effects (i.e., substantially complete energy deposition in the detector—the desired mechanism for a direct-conversion X-ray detector). With respect to the partial loss of energy in X-ray photons exhibiting the Compton effect, the energy lost due to the scatter event is a function of the deflection angle and initial energy. The higher portion of X-ray photons exhibiting Compton effects observed using silicon-based detectors results in worse energy resolution, making it difficult to determine the correct energy level of an X-ray photon based upon the observed deposited energy. By way of example, a silicon-based photon-counting detector may have about 66% Compton scatter in its detector response, which decreases spectral fidelity and dose efficiency.

In theory, a deconvolution approach may be used to recover the original spectrum from the detected spectrum, thus addressing losses attributable to the Compton effect. However, in practice, this approach is only possible if the detected spectrum has very high-energy resolution, beyond what is typically available in a clinical or non-laboratory setting. Thus, in practical applications, a silicon-based detector only has a limited number of energy bins for sorting and characterizing measurement events, which are insufficient for deconvolution-type algorithms.

The present approaches address these effects of Compton scatter in a silicon-based photon-counting X-ray detector in a different manner so as to extract useful information from the Compton-scattered photons. These techniques improve the dual- or multi-energy performance of silicon-based photon-counting detectors, such as computed tomography detectors or other suitable types of radiographic X-ray detectors.

With the preceding discussion in mind, FIG. 1 illustrates an embodiment of an imaging system 10 for acquiring and processing image data in accordance with aspects of the energy-discriminating, photon-counting approaches discussed herein. In the illustrated embodiment, system 10 is a computed tomography (CT) system designed to acquire X-ray projection data at multiple energy spectra (such as high- and low-energy spectra in a dual-energy context or multi-energy spectra in a photon-counting context); to process the projection data, including material decomposition for characterizing tissue or material type; and to reconstruct the projection data into volumetric reconstructions, for display and analysis. The CT imaging system 10 includes one or more X-ray sources 12, such as one or more X-ray tubes or solid state emission structures which allow X-ray generation at multiple spectra having different energy characteristics, during the course of an imaging session. For example, the emission spectra may differ in one or more of their mean, median, mode, maximum, or minimum X-ray energies.

By way of example, in one embodiment an X-ray source 12 (e.g., an X-ray tube) may be switched between a relatively low-energy polychromatic emission spectrum (e.g., X-ray tube operating voltage at about 80 kVp) and a relatively high-energy polychromatic emission spectrum (e.g., X-ray tube operating voltage at about 140 kVp). As will be appreciated, the X-ray source(s) 12 may emit at polychromatic spectra localized around energy levels (i.e., spectra comprising specific kVp ranges) other than those listed herein and/or at more than two emission spectra for a given examination. Selection of the respective energy levels for emission may be based, at least in part, on the anatomy being imaged and the materials of interest for tissue characterization.

In certain implementations, the source 12 may be positioned proximate to a filter assembly or beam shaper 22 that may be used to steer the X-ray beam 20, to define the shape and/or extent of a high-intensity region of the X-ray beam 20, to control or define the energy profile of the X-ray beam 20, and/or to otherwise limit X-ray exposure on those portions of the patient 24 not within a region of interest. In practice, the filter assembly or beam shaper 22 may be incorporated within the gantry, between the source 12 and the imaged volume.

The X-ray beam 20 passes into a region in which the subject (e.g., a patient 24) or object of interest (e.g., manufactured component, baggage, package, and so forth) is positioned. The subject attenuates at least a portion of the X-rays 20, resulting in attenuated X-rays 26 that impinge upon a detector array 28 formed by a plurality of detector elements (e.g., pixels) as discussed herein. As discussed herein, the detector 28 may be a photon-counting detector, including an energy-discriminating photon-counting detector, whose outputs convey information about the number and energy of photons that impact the detector at measured positions and over a time interval corresponding to a scan or imaging session. In certain such embodiments, the energy-discriminating, photon-counting detector may be a direct-conversion type detector (i.e., not employing a scintillator intermediary), such as a detector based on silicon strips.

Each detector element produces an electrical signal that represents the incident X-ray photons (e.g., the energy and number of incident photons) at the position of the detector element during an interval when the beam strikes the detector 28. Electrical signals are acquired and processed to generate one or more projection datasets. In the depicted example, the detector 28 is coupled to the system controller 30, which commands acquisition of the digital signals generated by the detector 28.

A system controller 30 commands operation of the imaging system 10 to execute filtration, examination and/or calibration protocols and may process the acquired data. With respect to the X-ray source 12, the system controller 30 furnishes power, focal spot location, control signals and so forth, for the X-ray examination sequences. In accordance with certain embodiments, the system controller 30 may control operation of the filter assembly 22, the CT gantry (or other structural support to which the X-ray source 12 and detector 28 are attached), and/or the translation and/or inclination of the patient support over the course of an examination.

In addition, the system controller 30, via a motor controller 36, may control operation of a linear positioning subsystem 32 and/or a rotational subsystem 34 used to move components of the imaging system 10 and/or the subject 24. The system controller 30 may include signal processing circuitry and associated memory circuitry. In such embodiments, the memory circuitry may store programs, routines, and/or encoded algorithms executed by the system controller 30 to operate the imaging system 10, including the X-ray source 12 and/or filter assembly 22, and to process the digital measurements acquired by the detector 28 in accordance with the steps and processes discussed herein. In one embodiment, the system controller 30 may be implemented as all or part of a processor-based system.

The source 12 may be controlled by an X-ray controller 38 contained within the system controller 30. The X-ray controller 38 may be configured to provide power, timing signals, and/or focal size and spot locations to the source 12. In addition, in some embodiments the X-ray controller 38 may be configured to selectively activate the source 12 such that tubes or emitters at different locations within the system 10 may be operated in synchrony with one another or independent of one another or to switch the source between different energy profiles during an imaging session.

The system controller 30 may include a data acquisition system (DAS) 40. The DAS 40 receives data collected by readout electronics of the detector 28, such as digital signals from the detector 28. The DAS 40 may then convert and/or process the data for subsequent processing by a processor-based system, such as a computer 42. In certain implementations discussed herein, circuitry within the detector 28 may convert analog signals of the detector to digital signals prior to transmission to the data acquisition system 40. The computer 42 may include or communicate with one or more non-transitory memory devices 46 that can store data processed by the computer 42, data to be processed by the computer 42, or instructions to be executed by image processing circuitry 44 of the computer 42. For example, a processor of the computer 42 may execute one or more sets of instructions stored on the memory 46, which may be a memory of the computer 42, a memory of the processor, firmware, or a similar instantiation.

The computer 42 may also be adapted to control features enabled by the system controller 30 (i.e., scanning operations and data acquisition), such as in response to commands and scanning parameters provided by an operator via an operator workstation 48. The system 10 may also include a display 50 coupled to the operator workstation 48 that allows the operator to view relevant system data, imaging parameters, raw imaging data, reconstructed data (e.g., soft tissue images, bone images, segmented vascular trees, and so on), material basis images, and/or material decomposition, and so forth. Additionally, the system 10 may include a printer 52 coupled to the operator workstation 48 and configured to print any desired measurement results. The display 50 and the printer 52 may also be connected to the computer 42 directly (as shown in FIG. 1) or via the operator workstation 48. Further, the operator workstation 48 may include or be coupled to a picture archiving and communications system (PACS) 54. PACS 54 may be coupled to a remote system or client 56, radiology department information system (RIS), hospital information system (HIS) or to an internal or external network, so that others at different locations can gain access to the image data.

Figure 2:
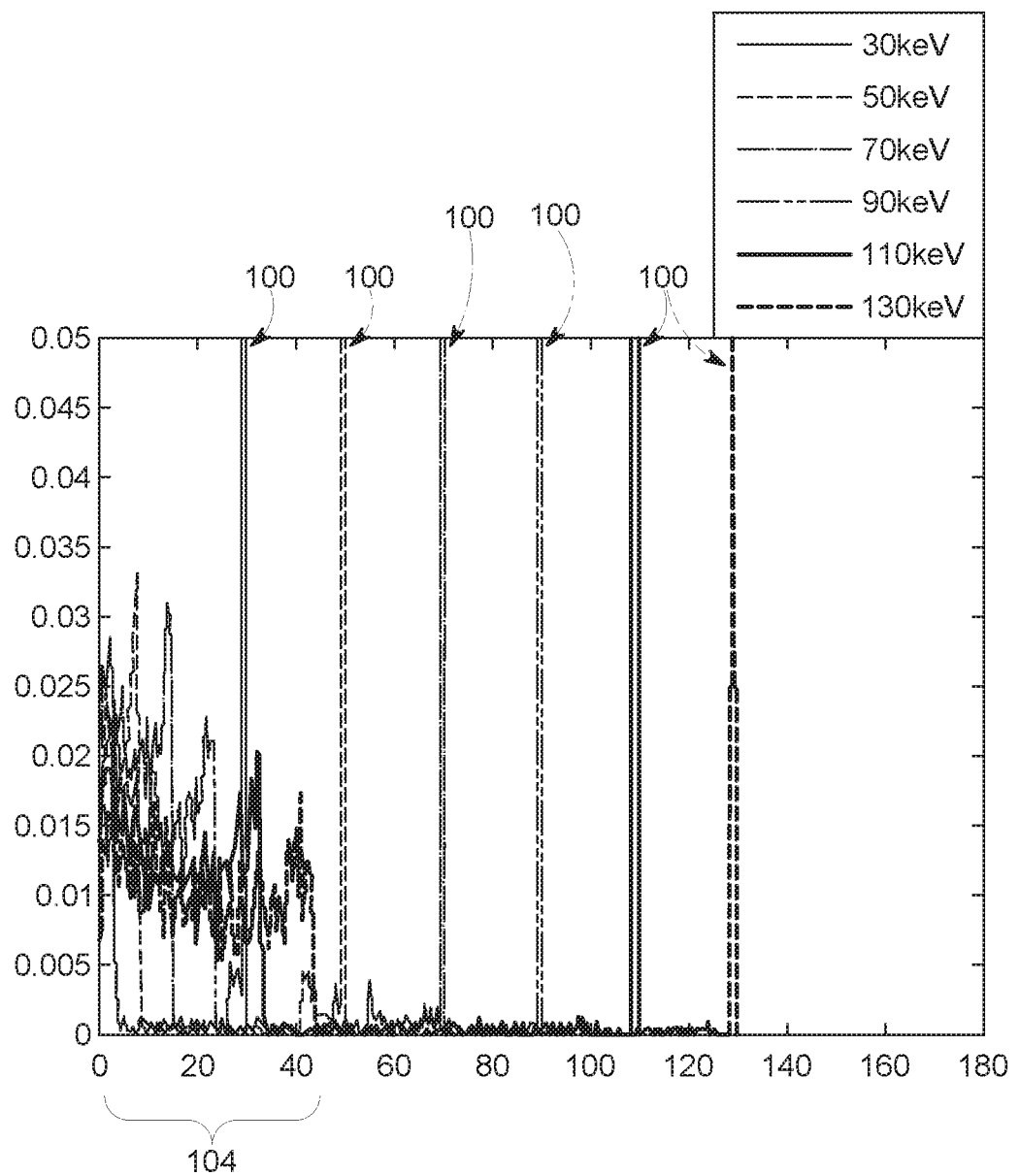
FIG. 2 depicts the spectral response of a silicon-based photon-counting detector at various incident energy levels, in accordance with aspects of the present disclosure.
Figure 3:
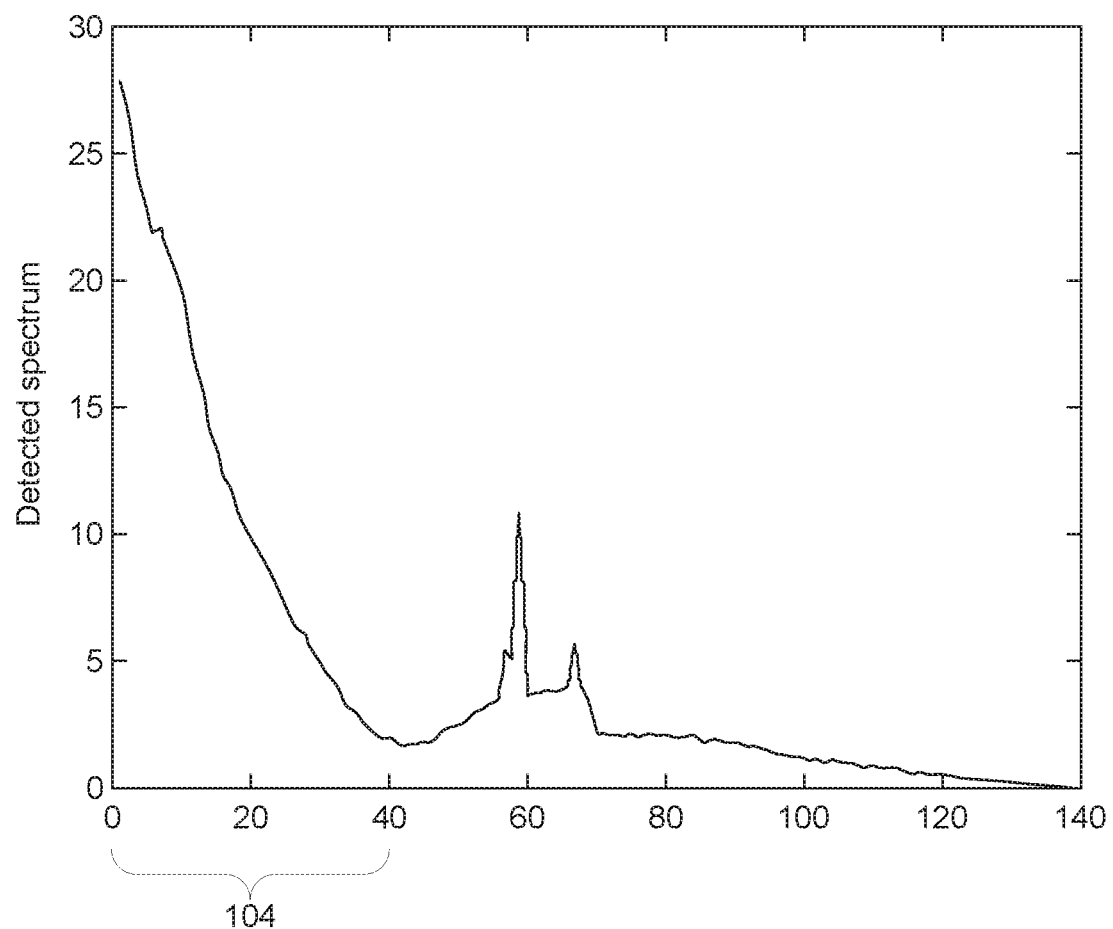
FIG. 3 depicts the detected spectrum at 140 kV after traversing 24 cm of water, in accordance with aspects of the present disclosure.

With the preceding discussion of an overall imaging system 10 in mind, and turning to FIGS. 2 and 3, a further explanation of spectral response is provided to establish further context for the present approaches that extract information from Compton-scattered X-ray photons. Turning to FIG. 2, the spectral response of a silicon-based photon-counting detector at several typical incident energy levels (e.g., 30 keV, 50 keV, 70 keV, 90 keV, 110 keV, and 130 keV) is depicted. Conversely, FIG. 3 depicts the detected Bremsstrahlung spectrum from an X-ray tube operated at 140 kVp, i.e., a common "high" energy spectrum in a dual-energy imaging context, for a scan of a 24-cm water phantom. As shown in FIG. 2, the spectral response function of a given incident energy consists of a peak or "delta pulse" 100 at the incident energy and a semi-constant plateau 104 at low energy that is caused by Compton scatter (i.e., higher-energy X-ray photons having "lost" some portion of their energy and deflected in scattering events, thereby being detected at the lower-energy end of the spectrum). This Compton scatter is the cause of the large portion of photons at low energy in the detected spectrum when using a silicon-based detector.

Turning to FIG. 3, the plotted spectrum of FIG. 3 is for a scan of a 24-cm water phantom when the X-ray tube is operated at 140 kVp. As may be appreciated, when the spectrum is attenuated by an imaged object, the Compton-scattered portion of the spectrum (i.e., the low- or less-energetic end of the spectrum) is better separated from the photoelectric portion (i.e., the high or more energetic end of the spectrum) since most of the low-energy photoelectric photons are absorbed by the object.

The following figures and discussion describe various approaches for handling the effects of Compton scatter in the context of a silicon-based photon-counting detector.

Figure 4:
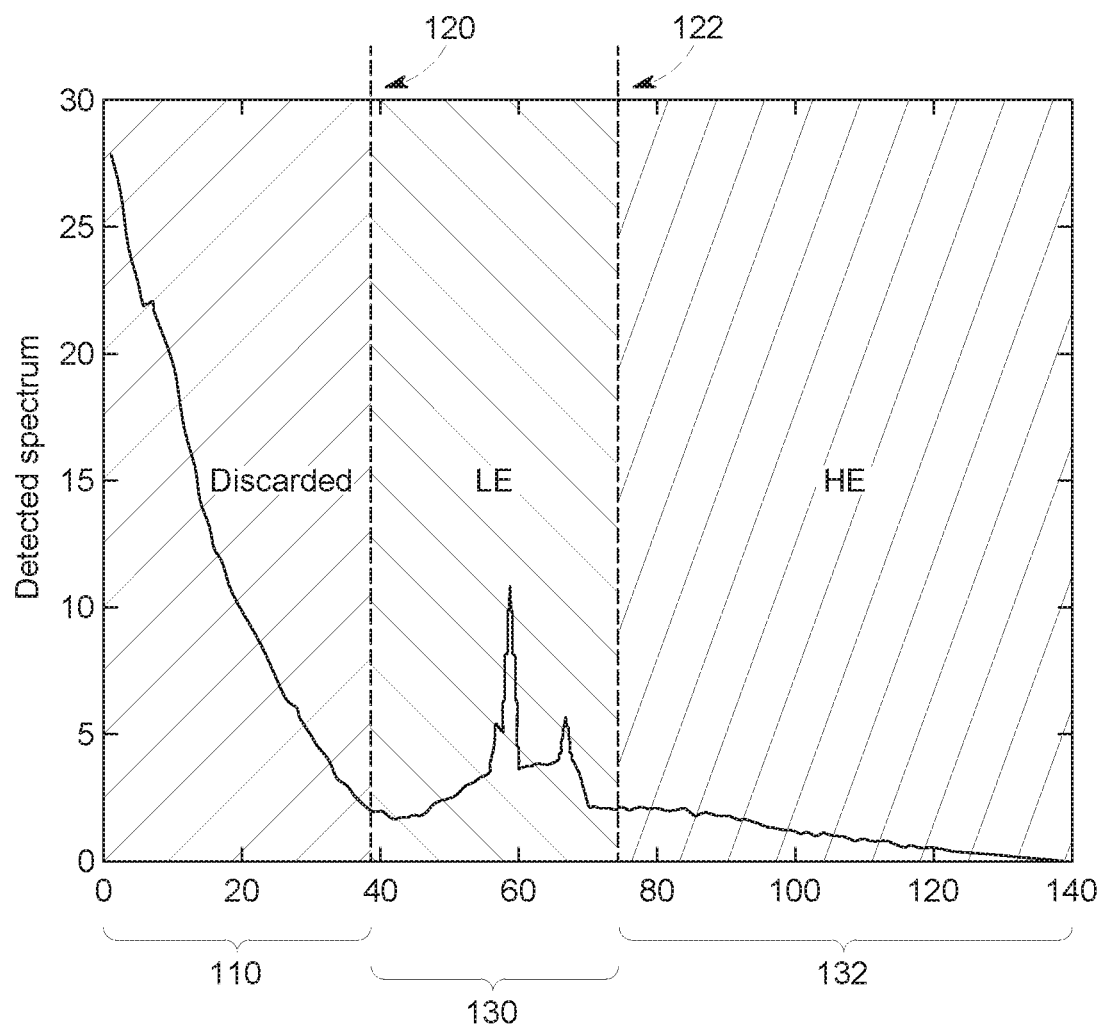
FIG. 4 depicts a first binning arrangement in which photon counts below a discard threshold are discarded from further operations, in accordance with aspects of the present disclosure.
Figure 5:
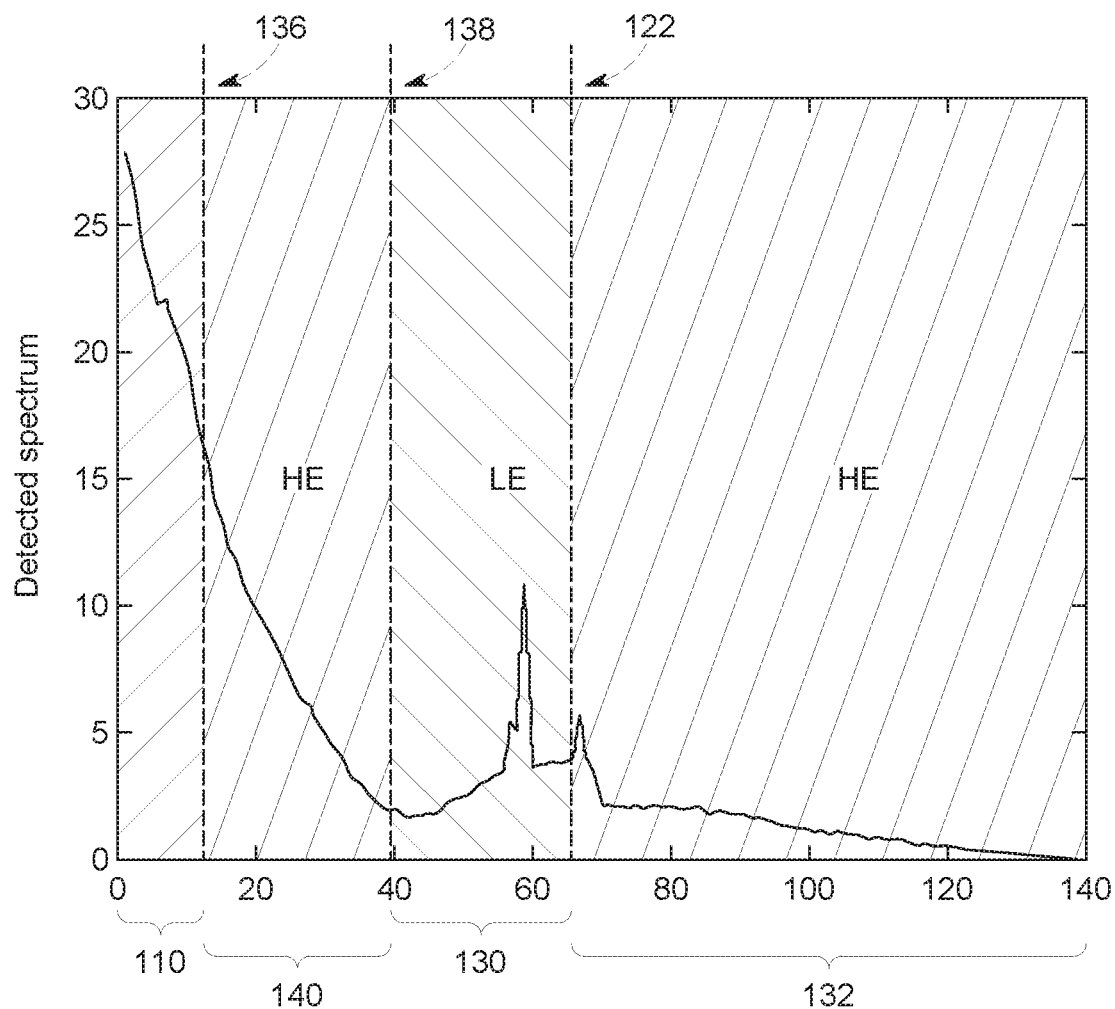
FIG. 5 depicts a second binning arrangement in which photon counts between a discard threshold and a Compton threshold are binned in a secondary high-energy bin for further operations, in accordance with aspects of the present disclosure.
Figure 6:
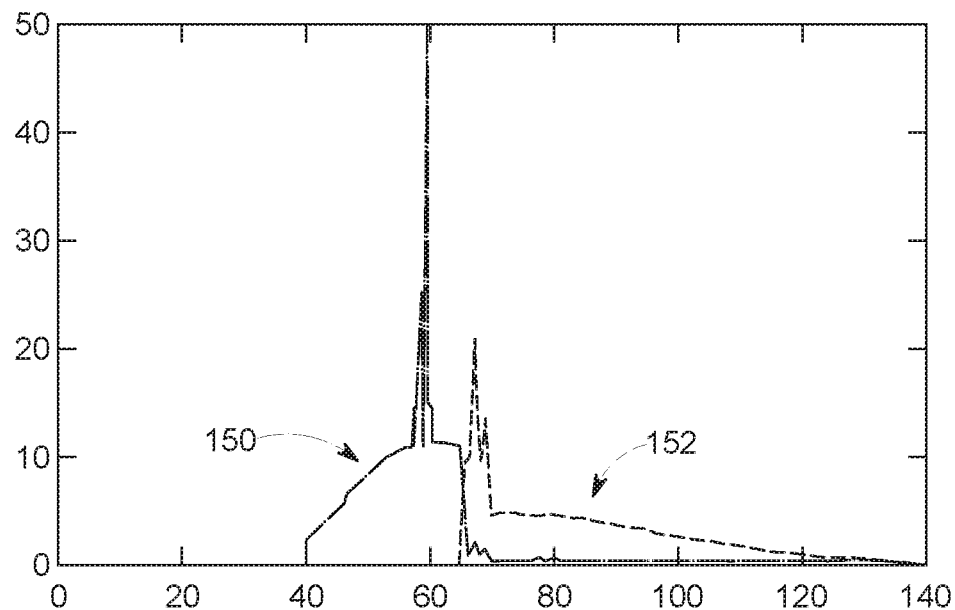
FIG. 6 depicts the spectra at low- and high-energy for discarded Compton scatter photons (leftmost graph) and for utilized Compton scatter photons (rightmost graph) in accordance with aspects of the present disclosure.
Figure 6:
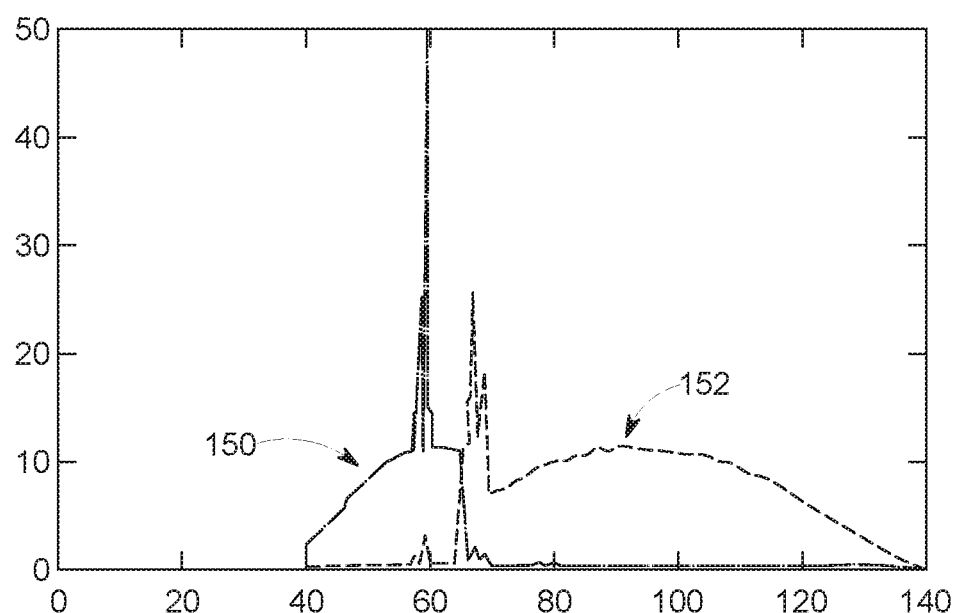

FIGS. 4-6 illustrate particular approaches for addressing Compton scatter photons in an acquired data set. In FIG. 4, all potential electronic noise and Compton scatter events (events below a selected discard threshold 120) are discarded (discard set or bin 110), which in this example consists of discarding a large number of all detected photons from further calculations and operations. The remaining observed photon counts are binned between a low-energy bin 130 and a high-energy bin 132 based on their observed energy relative to a specified low-energy/high-energy threshold 122.

Conversely, in FIG. 5 a binning strategy is employed in which a separate discard threshold 136 and Compton scatter threshold 138 are employed to distinguish between discardable electronic noise (discard bin 110) and Compton scatter events that may be recovered or binned to extract useful information. The discard threshold 136 may be determined as a function of the low-energy (LE)/high-energy (HE)

threshold 122, such as being the highest energy of Compton scatter observable at the energy level used as the threshold 122 to distinguish between primary high- and low-energy events. That is, the optimized discard threshold 136 may be characterized as the Compton edge of photons at the low-energy/high-energy threshold 122. Similarly, threshold optimization of the Compton threshold 138 and low-energy/high-energy threshold 122 may be accomplished by screening for the highest contrast-to-noise ratio (CNR) or dose-normalized contrast-to-noise ratio (CNRD). Compton threshold 138 may also be selected based on the highest-energy Compton scattering event possible resulting from the Compton scattering of the highest-energy photon in the X-ray beam, i.e. ~50 keV for a 140-keV photon for the spectrum shown in FIG. 3.

By way of example, in FIG. 5 if the energy threshold 122 to differentiate low- and high-energy photons is specified to be 65 keV, as shown in FIG. 5, then the discard threshold may be specified to be 13 keV which is the highest energy of Compton scatter from incident energy of 65 keV. Since the observed photons between 13 keV and the threshold 138 (here at about 40 keV, as in FIG. 4) are primarily or entirely caused by incidents of high-energy photons losing energy via Compton scatter events and being observed or measured as lower-energy Compton scattering events, photons observed in this bin (i.e., bin 140) may be counted as high-energy photons, effectively making a secondary high-energy bin 140 between the discard bin 110 and low-energy bin 130. The counts of the two high-energy bins may be combined and used in conjunction with the low-energy count data in the generation of one or more images, such as material-decomposition images, soft-tissue images, bone images, segmented vascular trees, and so forth.

This binning strategy has a significant impact on the spectral separation and the dose efficiency. FIG. 6 shows the spectra at low and high energy for discarded Compton scatter photons (leftmost graph) in accordance with the approach shown in FIG. 4 and utilized Compton scatter photons (rightmost graph) in accordance with the approach shown in FIG. 5. In these examples, the low- and high-energy spectra were obtained through 24 cm of water and with a Compton threshold of 40 keV. As shown, the low-energy spectrum 150 is unchanged, but the high-energy spectrum 152 where Compton scatter events are utilized is higher than where such events are discarded, resulting in substantially more useful detected high-energy events.

An imbalance between characterized low- and high-energy events may be observed from the binning approach shown in FIG. 5, which may be sub-optimal in material-decomposition contexts as such an imbalance may amplify the observed noise characteristics. However, shifting the energy threshold 122 higher is not a satisfactory solution to this imbalance between low- and high-energy flux because the discard threshold 136 will also be shifted higher accordingly, which means more photons are discarded. Thus, there may, in some circumstances, be a tradeoff between the balanced flux and dose efficiency.

Figure 7:
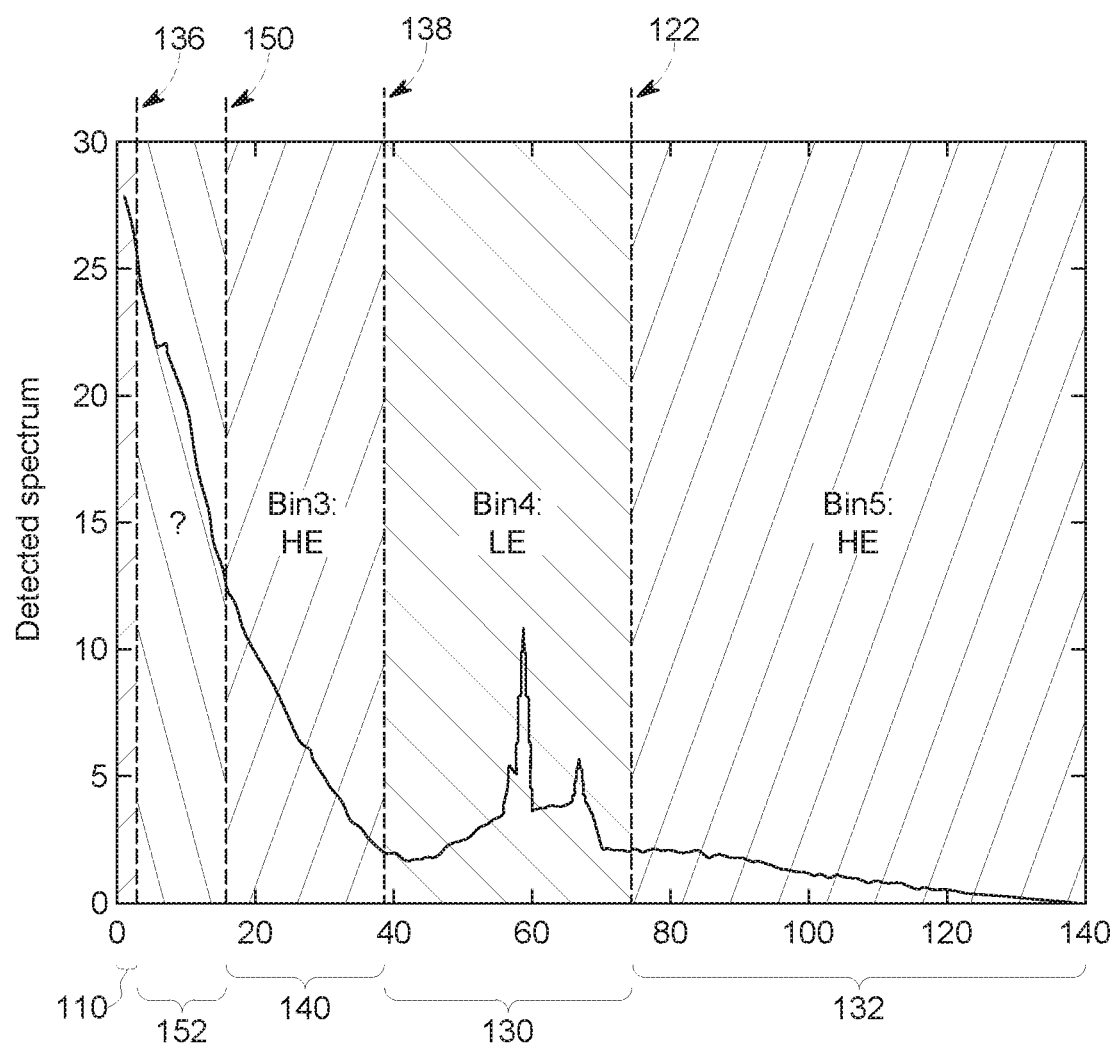
FIG. 7 depicts a third binning arrangement in which photon counts between an electronic noise threshold and a further threshold are binned in an unresolved energy bin for subsequent resolution, in accordance with aspects of the present disclosure.

To address this situation, an additional implementation may be employed. As shown in FIG. 7, in one example this further implementation increases the primary low-energy/high-energy threshold 122, such as to about 70-75 keV, and decreases the discard threshold to be just above the electronic noise; the threshold is denoted as the electronic noise threshold 136, such as to about 5 keV. The Compton edge 150, as determined based on the low-energy/high-energy threshold 122 as described above, is about 18-20 keV in these circumstances. Thus there is an unresolved or mixed energy bin 152 where the detected photons are from both low- and high-energy bins.

The mixture of low- and high-energy photons in unresolved bin 152 can be resolved using various approaches. In one implementation, the X-ray photons between the electronic noise threshold 136 to the Compton edge or threshold 150 of low-energy/high-energy threshold can be resolved using the spectrum shape and spectral response function, which may be derived from the X-ray photons that fall clearly within at least the primary high-energy and low-energy bins 130, 132. The corrected high-energy counts may be combined and used in conjunction with the corrected low-energy count data in the generation of one or more images, such as material-decomposition images, soft tissue images, bone images, segmented vascular trees and so forth.

Figure 8:
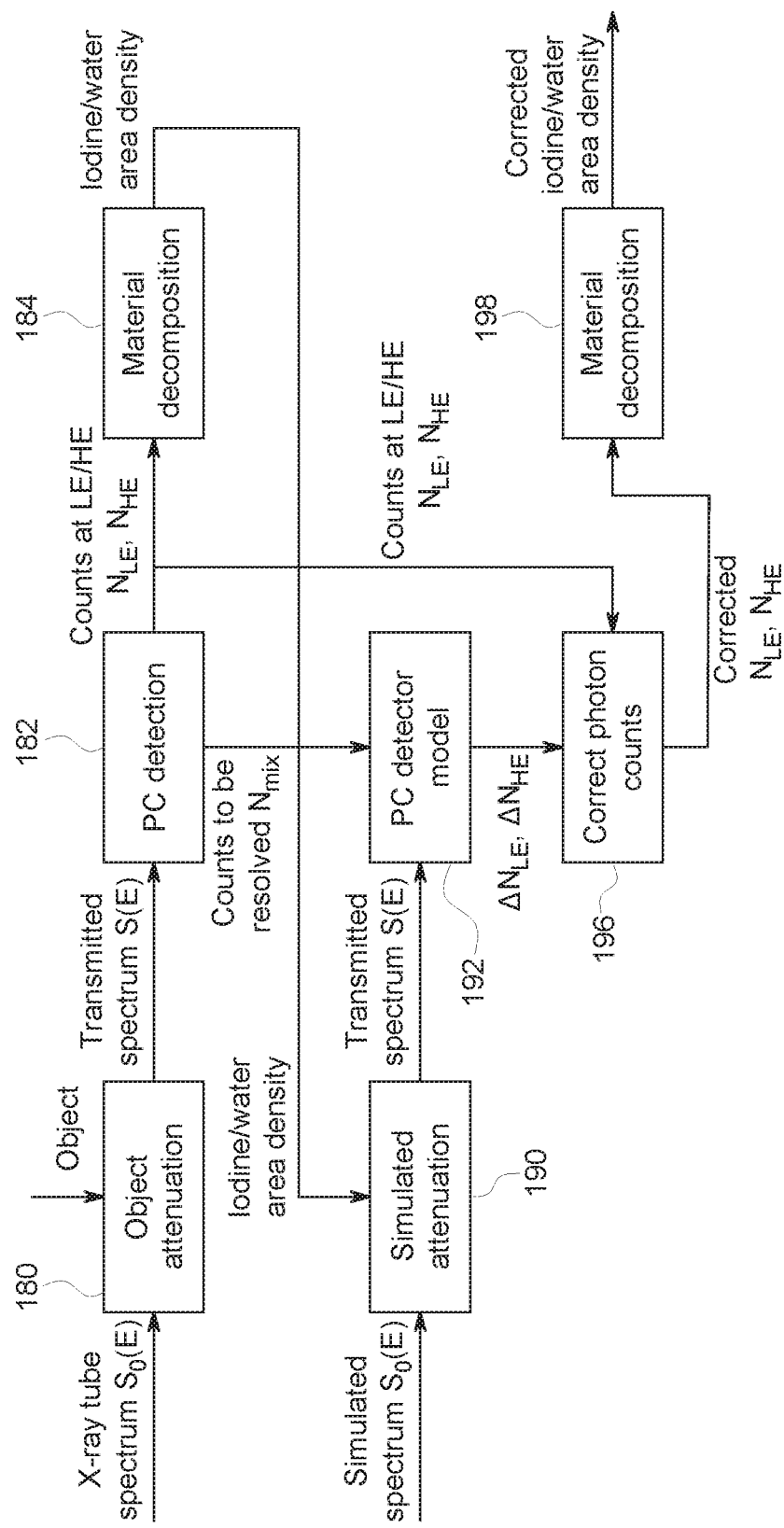
FIG. 8 depicts a process flow for resolving unresolved photon-counts, in accordance with aspects of the present disclosure.

By way of example, FIG. 8 depicts a flowchart depicting steps of one material decomposition approach that resolves the mixture of low- and high-energy photons of bin 152 using a forward model. In this approach, the measured data first undergo a standard material decomposition process discarding the data of bins 110 and 152 and deriving the area density of water and iodine, i.e. the projection data of the water and iodine density distributions. The measured counts in unresolved bin 152 is then resolved by feeding the water and iodine area density estimates into a forward model that emulates the detector response and the material-decomposition process to generate a correction term (i.e., a Δ). The resolved counts at low and high energy are then added back to the measured counts and the final material decomposition is performed based on the corrected counts in the low- and high-energy bins.

By way of more detailed explanation, the flowchart of FIG. 8 depicts an example where, based on an X-ray tube emission spectrum $S_0(E)$ and an object undergoing imaging, the X-ray spectrum is attenuated by the object (block 180), resulting in a transmitted spectrum S(E). The transmitted spectrum detected by photon-counting detection (block 182) and is processed so as to generate (such as based upon the binning operation described in FIG. 7) low-energy photon counts ($N_{LE}$), high-energy photon counts ($N_{HE}$), and photon counts to be resolved ($N_{mix}$).

In the depicted example, the low-energy photon counts ($N_{LE}$) and high-energy photon counts ($N_{HE}$) are used in a material decomposition process 184 that, among other outputs, yields an iodine area density estimate and a water area density estimate. A simulated spectrum $S_0(E)$ (which corresponds to the initial transmitted spectrum) is attenuated (block 190) based on the derived water and iodine area density estimates to determine a transmitted spectrum S(E) for the simulated transmission signal. The photon counts to be resolved ($N_{mix}$) may then, along with the simulated transmission spectrum, be provided as inputs to a photon-counting detector model 192 which, as an output, yields a correction for the low-energy and high-energy counts ($\Delta N_{LE}$ and $\Delta N_{HE}$), presumably an increase, to the low-energy photon counts ($N_{LE}$) and high-energy photon counts ($N_{HE}$) determined from the measured transmission data. The changes ($\Delta N_{LE}$ and $\Delta N_{HE}$) along with the low-energy photon counts ($N_{LE}$) and high-energy photon counts ($N_{HE}$) are provided as inputs to a photon-counting correction step 196 and corrected low-energy photon counts (corrected $N_{LE}$) and corrected high-energy photon counts (corrected $N_{HE}$) are determined. The corrected low-energy photon counts (corrected $N_{LE}$) and corrected high-energy photon counts (corrected $N_{HE}$) may then be provided as inputs to a material decomposition process 198 which, as one output, provides corrected iodine and water area density estimates.

Technical effects of the invention include a system including a silicon-based photon-counting detector where Compton scatter affects are addressed, such as by employing an additional high-energy bin between the low-energy bin and the bin of counts discarded and/or by resolving indeterminate Compton scatter photons using spectrum shape and/or the spectral response function.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An X-ray based imaging system, comprising:
    an X-ray source configured to emit X-rays at one or more energy spectra;
    an X-ray detector comprising a silicon-based direct-conversion material, wherein the X-ray detector is configured to generate signals in response to the transmitted X-rays during operation and wherein the signals correspond to photon counts observed at different energy levels for each exposure interval; and
    a processing component configured to receive the signals from the X-ray detector and to bin the photon count data for at least one respective energy spectrum based on observed energy levels into one of:
        a primary high-energy bin above a first threshold;
        a low-energy bin above a second threshold and below the first threshold;
        a secondary high-energy bin above a discard threshold and below the second threshold; and
        a discard bin below a discard threshold, wherein the discard threshold is based upon the highest energy of Compton scatter at the energy level corresponding to the first threshold;
    wherein the processing component is further configured to generate one or more images using high-energy photon counts derived for the primary high-energy bin and secondary high-energy bin and using the low-energy photon counts derived for the low-energy bin and discard the photon count data in the discard bin.

2. The X-ray based imaging system of claim 1, wherein the first threshold comprises a low-energy/high-energy threshold.

3. The X-ray based imaging system of claim 1, wherein the second threshold comprises a Compton threshold based on the highest energy in the X-ray beam.

4. The X-ray based imaging system of claim 1, wherein both the first threshold and the second threshold are set based upon the observed contrast-to-noise ratio (CNR) or dose normalized contrast-to-noise ratio (CNRD).

5. The X-ray based imaging system of claim 1, wherein the first threshold is set based upon the observed contrast-to-noise ratio (CNR) or dose-normalized contrast-to-noise ratio (CNRD).

6. The X-ray based imaging system of claim 1, wherein the second threshold is set based upon the observed contrast-to-noise ratio (CNR) or dose-normalized contrast-to-noise ratio (CNRD).

7. The X-ray based imaging system of claim 1, wherein the one or more images comprise material-decomposition images, soft-tissue images, bone images, or segmented vascular trees.

8. The X-ray system of claim 1, wherein the discard threshold comprises an electronic noise threshold.

9. The X-ray based imaging system of claim 8, wherein the processing component is further configured to bin the photon count data for the at least one respective energy spectrum based on observed energy level into an unresolved bin between the electronic noise threshold and a third threshold below the second threshold.

10. The X-ray based imaging system of claim 9, wherein the second and third thresholds define the secondary high-energy bin.

11. A method for resolving X-ray photon count data, comprising:
    acquiring a measured transmitted spectrum for an object by measuring transmission of X-ray photons through the object;
    determining a high-energy photon count by considering photons above a low-energy/high-energy threshold, and those photons undergoing Compton scattering and resulting in a detected energy above the Compton edge of the low-energy/high-energy threshold and below the Compton edge of the highest energy photon in the X-ray beam;
    determining a low-energy photon count by considering photons above the Compton edge of the highest energy photon in the X-ray beam and below the low-energy/high-energy threshold;
    discarding photons below a discard threshold below the Compton edge of the low-energy/high-energy threshold, wherein the discard threshold is based upon the highest energy of Compton scatter at the energy level corresponding to the low-energy/high-energy threshold; and
    performing material decomposition using the low-energy photon count and the high-energy photon count to generate a water area density estimate and an iodine area density estimate.

12. The method of claim 11, further comprising generating one or more images based on one or both of the water area density estimate or the iodine area density estimate.

13. The method of claim 11, wherein determining the low-energy photon-count and the high-energy photon-count comprises performing a binning operation on the measured transmitted spectrum.

14. An X-ray based imaging system, comprising:
    an X-ray source configured to emit X-rays at one or more energy spectra;
    an X-ray detector comprising a silicon-based direct-conversion material, wherein the X ray detector is configured to generate signals in response to the transmitted X-rays during operation and wherein the signals correspond to photon counts observed at different energy levels for each exposure interval; and
    a processing component configured to:
        receive the signals from the X-ray detector;
        determine a high-energy photon count by considering photons above a low-energy/high-energy threshold, and those photons undergoing Compton scattering and resulting in a detected energy above the Compton edge of the low-energy/high-energy threshold and below the Compton edge of the highest energy photon in the X-ray beam;

determine a low-energy photon count by considering photons above the Compton edge of the highest energy photon in the X-ray beam and below the low-energy/high-energy threshold;

discard photons below a discard threshold below the Compton edge of the low-energy/high-energy threshold, wherein the discard threshold is based upon the highest energy of Compton scatter at the energy level corresponding to the low-energy/high-energy threshold; and perform material decomposition using the low-energy photon count and the high-energy photon count to generate a water area density estimate and an iodine area density estimate.

15. The X-ray based imaging system of claim 14, further comprising generating one or more images based on one or both of the water area density estimate or the iodine area density estimate.

16. The X-ray based imaging system of claim 14, wherein determining the low-energy photon-count and the high-energy photon-count comprises performing a binning operation on the measured transmitted spectrum.

* * * * *